United States Patent [19]

Schneider et al.

[11] Patent Number: 5,308,619
[45] Date of Patent: May 3, 1994

[54] PHARMACEUTICAL AND ITS USE FOR THE TREATMENT OF STATES OF AGITATION AND NERVOUS DYSFUNCTIONS

[75] Inventors: Werner Schneider, Koblenz; Erich F. Elstner, Gröbenzell; Elisabeth Kleber, Oberschleissheim, all of Fed. Rep. of Germany

[73] Assignee: Steigerwald Arzneimittelwerk GmbH, Darmstadt, Fed. Rep. of Germany

[21] Appl. No.: 909,675

[22] Filed: Jul. 7, 1992

[30] Foreign Application Priority Data

Jul. 9, 1991 [DE] Fed. Rep. of Germany ....... 4122706

[51] Int. Cl.$^5$ ............................................. A61K 35/78
[52] U.S. Cl. ................................................... 424/195.1
[58] Field of Search ...................................... 424/195.1

[56] References Cited

PUBLICATIONS

R. F. Weiss: Lehrbuch der Phytotherapie, Hippokrates Stuttgart, 6. Aufl. 1985, Seiten 377, 355, 356.
H. A. Hoppe: Drogenkunde, Band 1, 8. Aufl., Walter de Gruyter, Berlin 1975, Seiten 472, 345, und 346.
Chemical Abstracts 111 (21) 187306e (1989).
Chemical Abstracts 96 (15) 115738w (1982).
Chemical Abstracts 95 (15) 129425H (1981).
Mem. Inst. Oswaldo Cruz Rio J. 86 (Suppl.) 1991, vgl. Computerauszug Biosis BA 93:32866.
Phytochemistry (OXF) 30 (9) 1991, vgl. Computerauszug Biosis BA 92:142436.
Yakugaku Zasshi 108 (5) 1988, vgl. Computerauszug aus Biosis BA 86:51996.
Arch. Int. Pharmacodyn Ther. 258 (1) 1982, vgl. Computerauszug aus Biosis VA 76:74944.

*Primary Examiner*—John W. Rollins
*Attorney, Agent, or Firm*—Sughrue, Mion, Zinn, Macpeak & Seas

[57] ABSTRACT

The invention concerns a pharmaceutical and its use for the treatment of states of agitation and nervous dysfunctions, which comprises as active ingredients extracts of Corydalis and Eschscholtzia obtained by alcohol extraction (2.5:10), optionally together with conventional additives, the weight ratio of the extract Eschscholtzia to Corydalis being in the range from 20:1 to 1:1.

13 Claims, 12 Drawing Sheets

Fig.1

Survey of the catecholamine metabolism

PHARMACEUTICAL AND ITS USE FOR THE TREATMENT OF STATES OF AGITATION AND NERVOUS DYSFUNCTIONS

FIELD OF THE INVENTION

The invention concerns a pharmaceutical and its use to ameliorate states of agitation and nervous dysfunctions.

BACKGROUND OF THE INVENTION

It is known that the interim and end products of the catecholamine metabolism have an influence on the state of agitation in human beings. Thus, for example, the end product adrenalin acts as a neurotransmitter of the adrenergic nervous system on alpha- and also on beta-receptors. As a sympathicomimetic agent, adrenalin increases the contraction force of the heart. Because adrenalin furthermore increases the oxidative metabolism in the cells, on the whole it causes an increased readiness of the organism for action. Correspondingly one also observes an increase of the adrenalin release in stress situations. Especially high concentrations of adrenalin as well as of its precursor, noradrenalin, may have the result of excess agitation, nervousness and therefore deficient performance capability of the body, whereas only slightly increased values of these amines have a very positive effect: the pulse rate and blood pressure are slightly increased, the muscles and brain are stimulated, the receptivity is raised.

Furthermore it is known that disturbances in the concentration of dopamine, a further precursor of adrenalin, may lead to states of agitation and nervous dysfunctions. In particular, depression may occur in the case of a lack of dopamine. A special dopamine deficiency syndrome is Parkinsonism, whose partial symptoms include akinesis, rigidity and passive tremor. Recent clinical results show evidence of a therapeutical activity of dopa when treating Parkinsonism; this effect appears to be understandable because of the observed dopamine reduction in the basal ganglia.

Therefore it is desirable in a case of dopamine deficiency to increase by natural means the concentration of this catecholamine. This can be achieved by increasing on the one hand the dopa/dopamine synthesis and on the other, by preventing dopamine decomposition.

The object of the present invention is to make available a pharmaceutical which increases the dopamine concentration of a patient in natural metabolism.

The object above is achieved in accordance with the invention by a pharmaceutical which is characterized in that it comprises as active ingredients extracts obtained by alcohol extraction (2.5:10) of Corydalis and Eschscholtzia, optionally together with the conventional additives, wherein the weight ratio of the extracts Eschscholtzia to Corydalis is in the range from 20:1 to 1:1.

The invention comprises additionally the use of the inventive pharmaceutical for the amelioration and/or suspension of states of agitation and nervous dysfunctions, which are based on a disturbance of the amine balance, particularly on a reduced concentration of dopa/dopamine.

The subject of the invention is furthermore the use of an extract obtained by alcoholic extraction (2.5:10) for the treatment and/or or for the preparation of a pharmaceutical for the treatment of states of agitation and nervous dysfunctions, which are based on a disturbance in the amine balance, in accordance with the present invention.

DETAILED DESCRIPTION OF THE INVENTION

The inventive pharmaceutical can contain the extracts obtained by alcohol extraction in the form of a freeze-dried powder, an aqueous and/or an alcohol solution. The preparation of the freeze-dried powder is performed as a rule by freeze-drying the extract (drug extract) obtained by alcohol extraction in accordance with the freeze-drying processes which are conventional per se.

The freeze-dried extracts of Corydalis and Eschscholtzia can be stored separately or in a mixture, and optionally for the preparation of the pharmaceutical they can be mixed with a suitable pharmaceutic carrier substance/diluent. To prepare tinctures, water and/or alcohol are particularly suitable. Primarily the pharmaceutical contains the active ingredients in the form of an extract obtained by alcohol extraction (2.5:10) and in particular it consists of such a drug extract.

The ratio of Eschscholtzia to Corydalis (based on the weight of the dry extract) is preferably in the range from 10:1 to 2:1, and in particular amounts to 4:1.

In accordance with the invention preferably extracts of *Corydalidis cavae rhizome* and *Eschscholtzia californicae herba* are used as the active ingredient.

The inventive pharmaceuticals are present in a conventional form for oral administration, especially in the form of tablets, dragees, capsules or primarily tinctures. The preparation of these forms of administration is performed optionally when using the pharmaceutical dilution and/or carrier substances conventionally used and suitable for the individual administration forms, in the manner known per se, e.g. by forming tablets, pills, encapsulation of the extract present in freeze-dried form or an alcoholic and/or aqueous solution thereof. To prepare liquid administration forms, such as especially tinctures, preferably the alcohol drug extracts obtained by alcohol extraction are used directly. Apart from freeze-drying of these alcohol extracts it is also possible for the preparation of the freeze-dried extracts to evaporate the alcohol drugs extract directly, preferably in a vacuum and/or in an inert gas atmosphere until they are dried, and to process further the residue thus obtained into the desired form of administration.

The concentration of the active ingredients in the inventive pharmaceutical can be varied in broad limits. As a rule, the concentration is 0.5 to 20% by weight based on the finished pharmaceutical composition, and in particular 1 to 10% by weight, and primarily 1 to 4% by weight. When the alcohol drug extract obtained by alcohol extraction (2.5:10) is used, it is preferably employed in the concentration which is obtained directly after extraction; the extracts from Corydalidis and Eschscholtzia are used especially in such a ratio that the ratio of Corydalis to Eschscholtzia corresponds to the ratios named above as preferred.

For the preparation of the individual extracts of Corydalis and Eschscholtzia, especially of *Corydalis cavae rhizoma* and *Eschscholtziae californicae herba*, drugs are used which correspond to the specifications of DAB 9. This is ensured by quality control when obtaining the drug.

The preparation of the individual extracts is carried out in a manner known per se in accordance with the conventional and standardized extraction processes, such as e.g. by maceration or percolation using ethanol or ethanol/water mixtures. A drug-extract ratio of 2.5:10 is maintained, i.e. 10 ml of drug extract are obtained from 2.5 g of the drug. Preferably 30% by volume ethanol is used as the extraction agent. The preparation can be regulated on the basis of in process control.

For the judgement and ascertainment of the constant quality of the extracts, the conventional quality criteria are adduced. In particular, the total spectra of the extracted substances are used for this purpose and on the other hand, the analyses of the main alkaloids of the two drugs (cf. e.g. . . . ) which are known from the literature.

The extracts which are released after the quality control then correspond to the desired administration form and concentration, and are further processed as a liquid or freeze-dried extract.

The type and amount of administration is oriented especially towards the gravity of the disease, the general state and the age of the patient. As a rule, the administration quantity in the form of a tincture, which is preferred according to the invention, amounts to 2 drops/kg body weight, once or several times per day. In the form of other oral administration forms, as a rule corresponding amounts are administered, preferably 2 to 5 mg of total dry extract/kg body weight, once or several times each day.

BRIEF DESCRIPTION OF THE DRAWINGS

The figures enclosed have the following significance.

Figure 1:
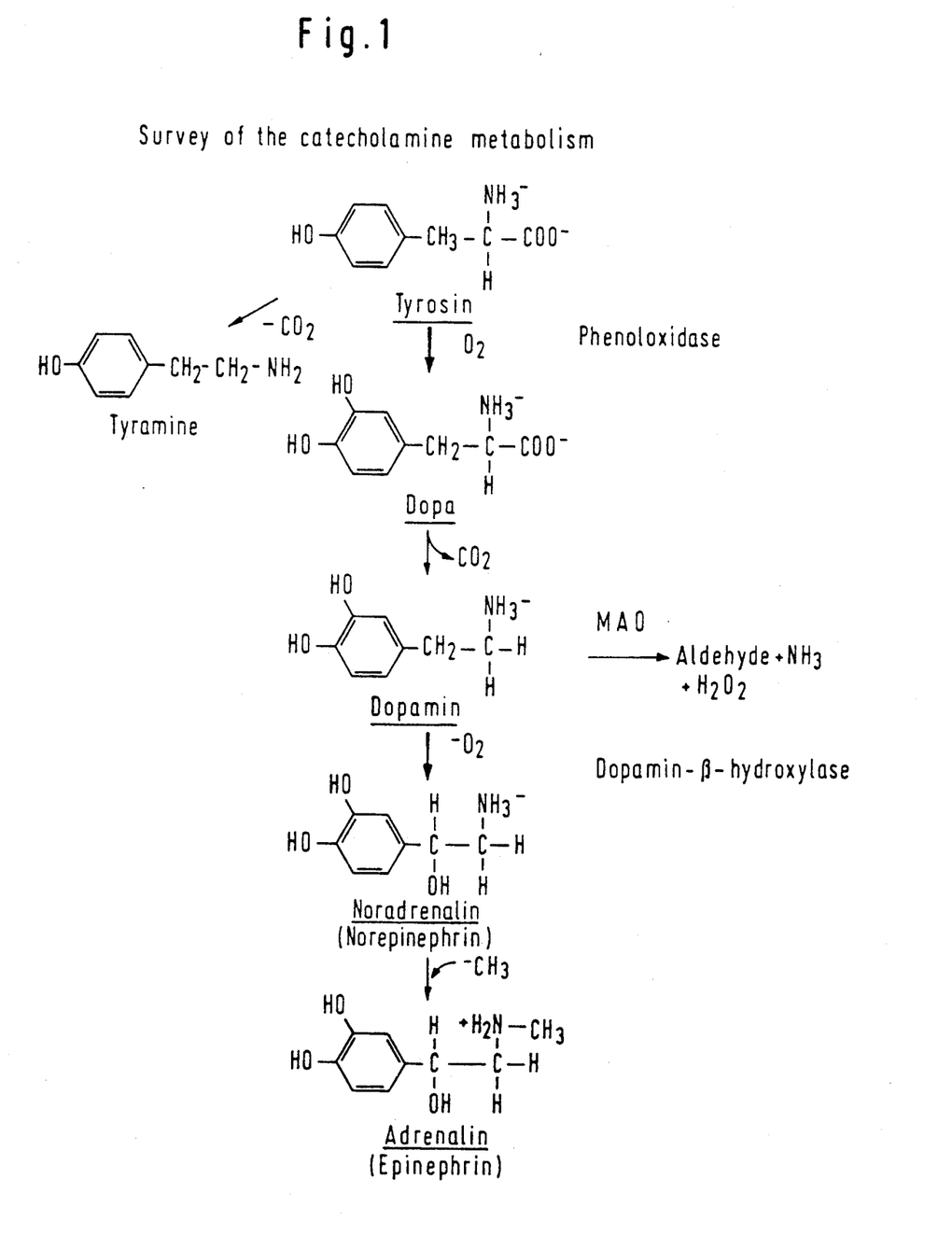
FIG. 1 shows the metabolism plan of the catecholamine synthesis.

FIG. 1 shows the metabolism diagram of catecholamine. The compounds dopa and dopamine which arise are dependent as to their concentration on the one hand as to how fast the conversion of tyrosin into dopa takes place, and on the other on the speed at which dopamine further reacts to noradrenalin and adrenalin. In addition, dopamine is also subject to decomposition by mono-amino oxidases (MAO), so that thereby its concentration in the metabolism can be notably influenced.

As can be inferred from FIG. 1, an increased dopamine concentration is obtained when the reaction of the phenoloxidase (phenolase, tyrosinase) can be increased, and the influence of dopamine-$\beta$-hydroxylase as well as of mono-amino oxidases can be reduced.

Experiments were carried out below, which show in what degree the active components of the inventive pharmaceutical influence the three enzyme reactions.

The following investigations were, unless otherwise stated, carried out with enzymes obtainable on the market and with *Corydalidis cavae rhizoma* and *Eschscholtziae californicae herba*.

EXAMPLES

1. Investigation of the tyrosinase reaction:

Tyrosin is hydroxylated in the metabolism in an oxygen-consuming reaction into L-dopa. This first step of the catecholamine synthesis is catalysed by a tyrosinase or phenolase or phenoloxidase, which constitutes a copper-containing enzymen enzyme with low specificity.

It is known that phenolases are wide-spread in nature, and occur in plants, fungi and in various animal tissues. They play an important part everywhere where mono- or diphenols are oxidized, while in many cases oxidative polymerization steps are initiated, such as e.g. the formation of lignin or melanin.

Phenolases catalyse two consecutive oxidation steps which can be described as follows:

1. The 'cresolase activity' of the enzyme causes the hydroxylation of a monophenol in the ortho-position, forming a diphenol.
2. The 'catecholase activity' catalyses the further oxidation of the resultant o-diol into the corresponding quinone.

Both reactions are directly dependent on each other. The close connection of the cresolase and catecholase reaction is based on the oxidation status of the copper atom in the active center, which according to D. Kertesz and R. Zito in O. Hayaishi (editor) "Oxygenases", Academic Press, London (1962), Chapter 8, Phenolase, is shown as follows:

(Cu$^{++}$)$_2$-enzyme + o-dihydroxyphenol → (Cu$^+$)$_2$-enzyme + o-quinone + 2 H$^+$;

(Cu$^+$)$_2$-enzyme + 0.5 O$_2$ + 2 H$^+$ → (Cu$^{++}$)$_2$-enzyme + H$_2$O

In the electron balance above of the copper, the cresolase reaction is not considered. In fact, it does not appear to be clear whether the hydroxylation of the monophenol is catalysed by a genuine enzyme reaction or whether this reaction takes place chemically in parallel with the catechinoxidation in accordance with the following scheme:

o-quinone + monophenol + H$_2$O → 2 o-diphenol.

Evidence for the hypothesis of a non-enzymatic reaction is provided primarily by the fact that in the reaction of monophenols with phenolases, an induction phase is observed which may last up to one hour in the case of tyrosinases from animal tissue. A continuous enzyme reaction can only take place if dioles or quinones are present as an impurity or have arisen due to "autoxidation".

Figure 2:
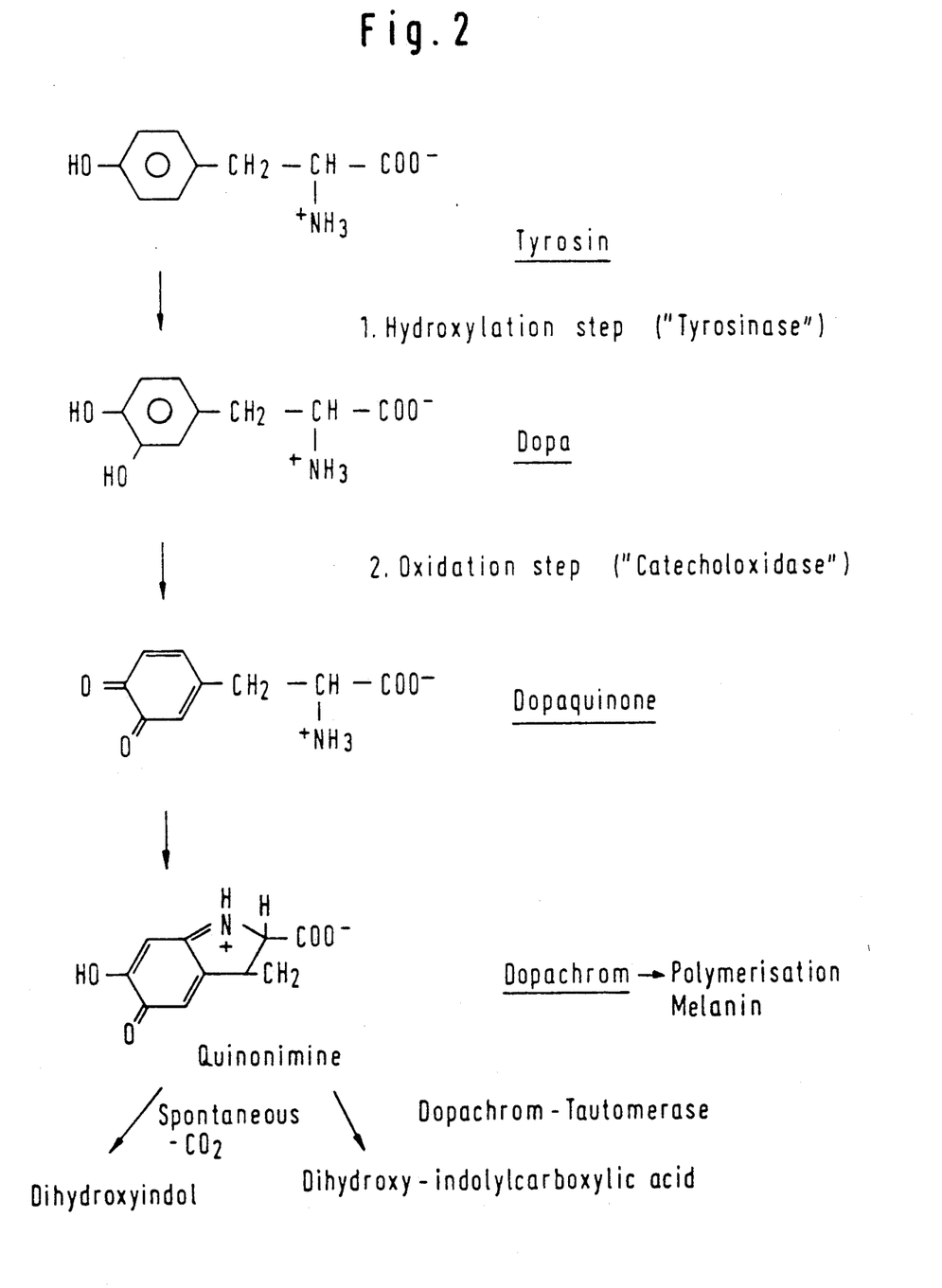
FIG. 2 shows a schematic survey of the reaction plan of tyrosin via dopa, dopaquinone into dopachrome or melanine.

Investigation of the Tyrosinase Reaction With Plant Extracts From Corydalis and Eschscholtzia FIG. 2 shows schematically the reaction diagram, proceeding from tyrosin, to dopachrome and its conversion into quinonimin or melanin.

Then the oxidation of tyrosin to dopachrome (FIG. 2), the first oxidation product of dihydroxyphenylalanine (dopa), was observed experimentally. Dopachrome itself is a substrate for a 'dopachrome tautomerase' and is a precursor of the melanin formation. Both the formation of dopachrome as well as the melanin synthesis lead to a decompositon of dopa and thus to a reduced synthesis of dopamin.

The dopachrome concentration can be followed in the UV spectrum at a wavelength of 303-318 nm. Its formation from tyrosin is equated with the activity of the phenolase to be investigated, which is regarded as determining the speed.

The investigations were carried out on the following substrate mixtures:

2 mM tyrosin
100 mM phosphate buffer, pH 6.5
20 U tyrosinase or alcohol extracts of Eschscholtzia and/or Corydalis, diluted in the ratio 1:10,000 (proceeding from the basic extract as in the following example).

Figure 3:
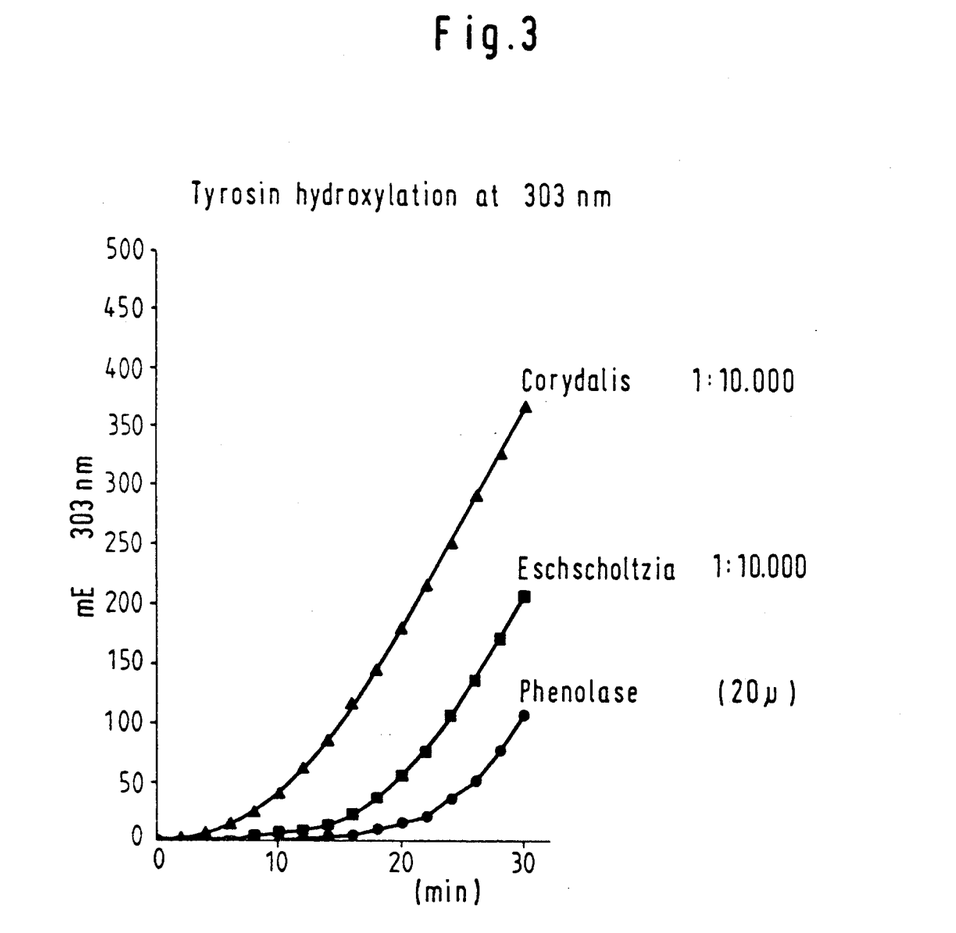
FIG. 3 shows the tyrosin hydroxylation determined by UV-spectrometry at 303 nm in the presence of Corydalis extract 1:10,000, Eschscholtzia extract 1:10,000 or 20 units phenolase.

FIG. 3 shows the tyrosin-hydroxylation determined by UV spectrometry at 303 nm in the presence of a phenoloxidase or extracts from Corydalis and Eschscholtzia. Only in the presence of phenolase is the appearance of a 'lag phase' of about 15 minutes observed.

Dilutions from Corydalis extracts up to 1:10,000 lead to a clear reduction of this lag phase or initial phase, as follows from FIG. 3. With higher concentrations of Corydalis, the immediate onset of the maximal conversion rate without a 'lag phase' is observed.

The extract of Eschscholtzia also leads to a shortened initial phase; but the activity of the Eschscholtzia extract is clearly below that of Corydalis.

Control tests have shown that the presence of corresponding amounts of ethanol have no influence on the reaction. In addition, tests with pyrroloquinolinquinone (PQQ) showed that the addition of this physiologically very interesting quinone has no influence on the initial phase of the phenolase reaction. Hypericin, which as a paraquinone could possibly influence the lag phase, also has no influence on the reaction.

In this test series, the fact is interesting that the extract of Corydalis indeed clearly brings forward the time of the maximal conversion rate of tyrosin, but has no influence on the maximal conversion rate. Tests with different substrate concentrations show in the Lineweaver-Burk-plot no displacement of the $K_m$ value of the phenolase reaction (see FIGS. 4a to 4f).

For further clarification of the mechanism of the tyrosinase reaction, particularly as regards a shortening of the lag phase, further substances were added to the test batch:

a) The addition of copper salts had no influence on the enzyme reaction.
b) Ascorbic acid as a reducing agent can prevent the lag phase in various reaction types, as is known from the literature. But within the present test series, this could not be observed: ascorbic acid may in fact initiate the conversion of tyrosin to L-dopa, but it prevents simultaneously its further oxidation to dopachrome. A phenolase reaction could not be observed in the presence of ascorbic acid at 303 nM over a period of 30 min.; the 'lag phase' was possibly even prolonged.
c) A combination of PQQ with ascorbic acid, wherein the reduced form $PQQH_2$ results, which could influence the reaction as a diol, also caused an extension of the lag phase.
d) The addition of 'genuine' diols, such as 3,4-dihydroxybenzene and D,L-dopa, shortens the lag phase of the reaction (in the case of the dopa addition, the speed of the dopachrome formation is also increased by the increased substrate offered).

Figure 5:
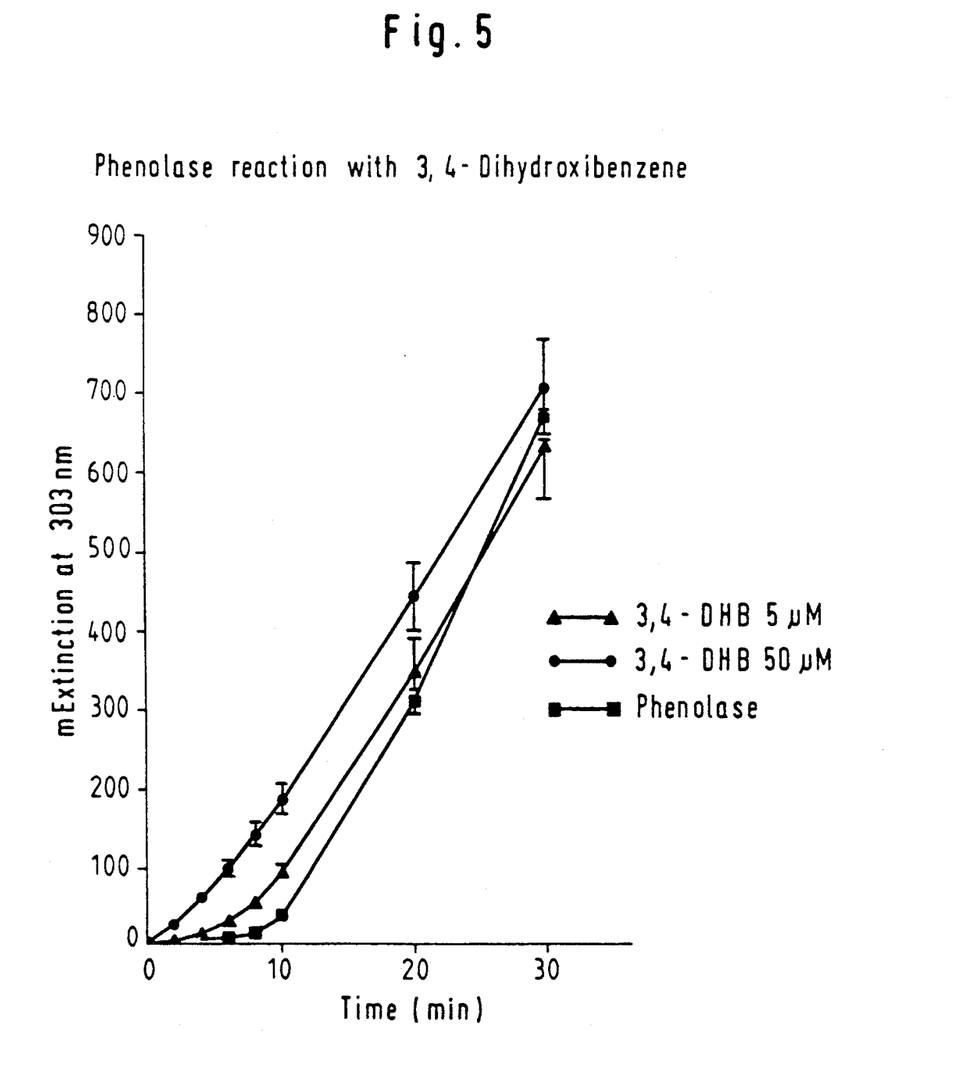
FIG. 5 reflects the phenolase reaction in the presence of 3,4-dihydroxybenzene.
Figure 6:
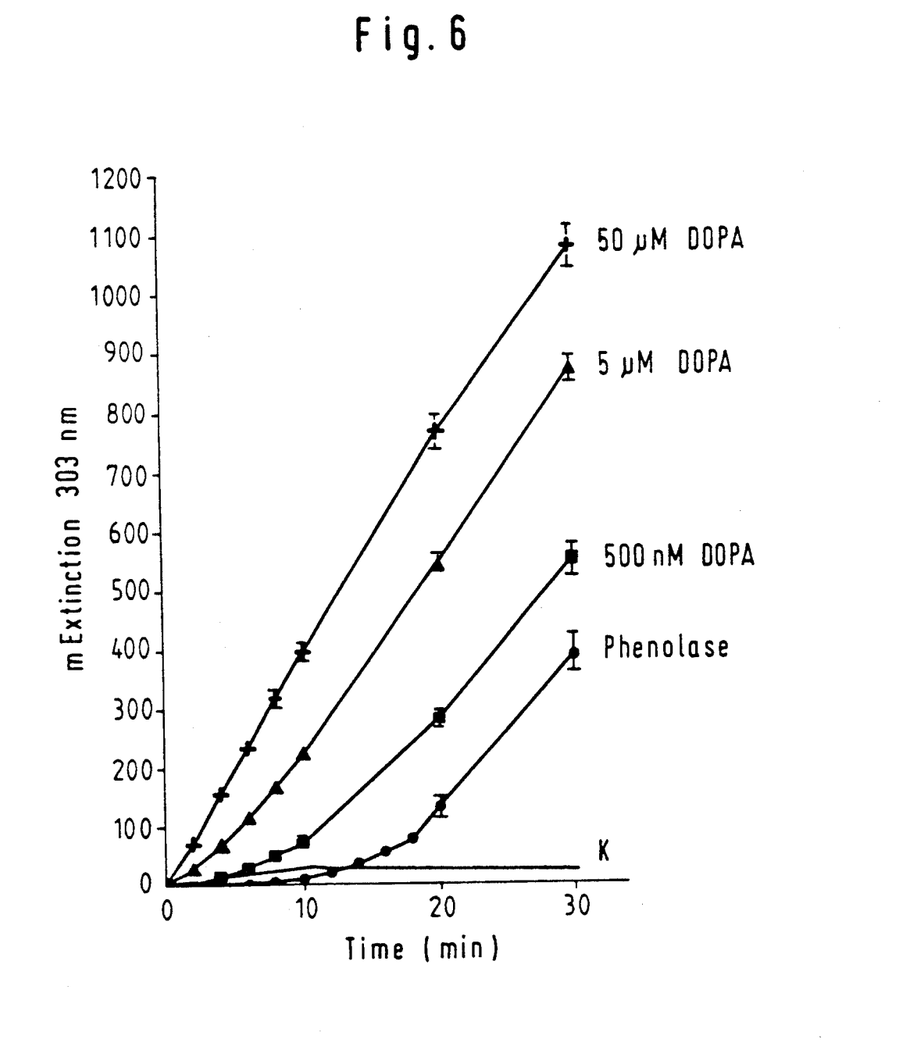
FIG. 6 shows the influence of D,L-dopa on the phenolase reaction with different dopa concentrations (K = control).

In FIG. 5, the phenolase reaction is reproduced in the presence of 3,4-dihydroxybenzene. FIG. 6 shows the influence of D,L-dopa on the phenolase reaction depending on the dopa concentration. The influence of the named diols on the lag phase can clearly be inferred from FIGS. 5 and 6.

An autoxidation of dopa, which takes place at alkaline pH values, is not observed or only slightly at pH 6.5.

The tests above show that a reduction of the time in the initial phase of the phenolase reaction can only be achieved by the addition of diols. Quinoline and ascorbic acid show no influence. It must therefore be assumed that the extracts of Corydalis and Eschscholtzia contain ortho-diols, which produce an immediate conversion of tyrosin into dopa. It should further be assumed that the extracts of Corydalis and Eschscholtzia also lead in vivo to a faster conversion of tyrosin and thus to an increased concentration of dopa.

2. Investigation of the dopamin-$\beta$-hydroxylase reaction:

The enzyme dopamin-$\beta$-hydroxylase catalyses the conversion of dopamin to noradrenalin. Dopamin-$\beta$-hydroxylase is also an enzyme containing copper. The hydroxylation takes place with oxygen consumption and requires ascorbic acid and fumarate as reducing agents, to regenerate the oxydation status of the copper atom.

The activity of the enzyme is determined by potentiometry based on the consumption of molecular oxygen. The respective test batch contains the following components:

respectively 100 $\mu l$ tyramine, fumarate, ascorbate (each 5 mM)
1 ml phosphate buffer, pH 5 (100 mM)
1 ml water
100 $\mu l$ enzyme (corresponding to 0.1 U).

The oxygen consumption rates were computed on the basis of the $O_2$ content of a 37° C. solution with the respective volumes.

When adding Eschscholtzia extract, a clear, concentration-dependent inhibition of the enzyme reaction is shown, i.e. the side chain hydroxylation is largely prevented. It was observed that the enzyme activity is also inhibited by ethanol. But the inhibition of the extract is substantially greater, so that here a clear difference can be made.

Figure 7:
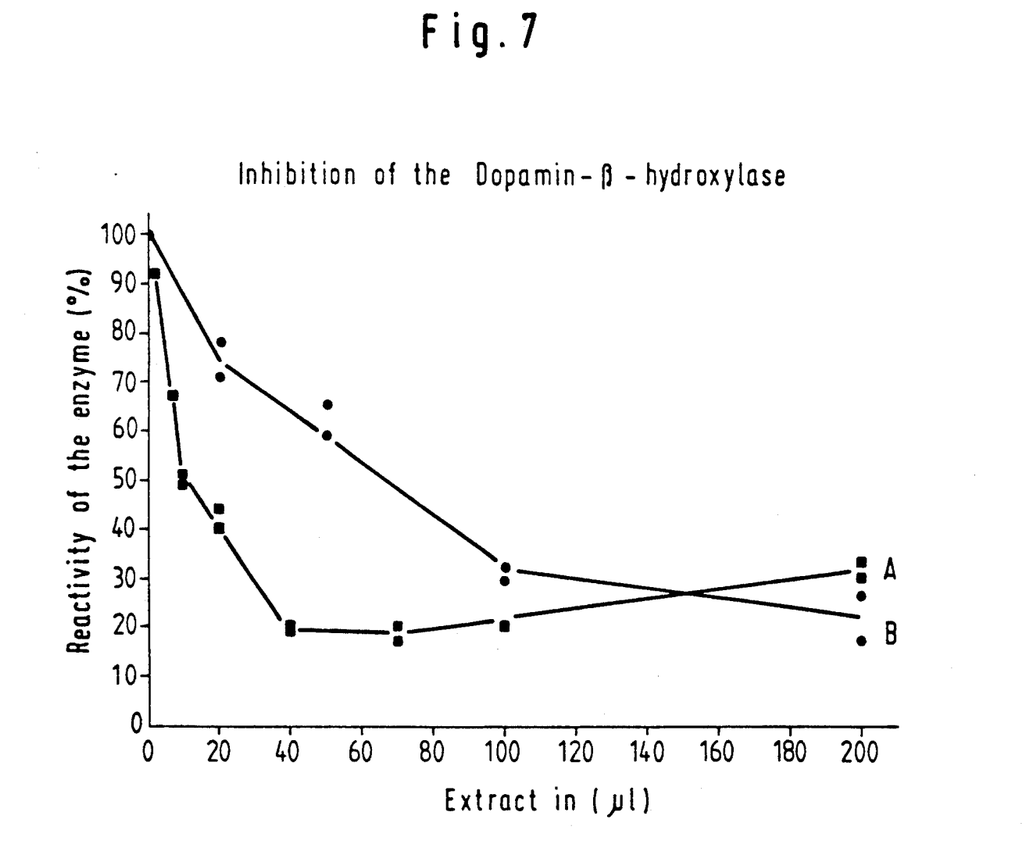
FIG. 7 shows the inhibition of dopamine-$\beta$-hydroxylase by Eschscholtzia extract (curve A) as well as an aqueous 1% solution of the freeze-dried extracts of Corydalis and Eschscholtzia (curve B).

FIG. 7 shows the inhibition of the dopamin-$\beta$-hydroxylase by Eschscholtzia extract (curve A) as well as of an aqueous 1%-solution of the freeze-dried extract of Eschscholtzia and Corydalis in the ratio 20:1 (curve B) according to the invention.

In FIG. 7, both curves show a clear inhibition of the enzyme activity. Differences in the curves may be due to the presence or absence of ethanol as well as of Corydalis extract (curve B). The decreasing effect of the enzyme inhibition when using Eschscholtzia extract can be traced back partly to an oxygen consumption by the different substrates of the extract. The aqueous solution of freeze-dried extracts of Corydalis and Eschscholtzia indeed show an oxygen consumption with tyramine, ascorbate and fumerate; but the inhibition effect on the enzyme does not fall off, whereby an interpretation of the effect is substantially complicated.

The tests above show clearly that the enzyme dopamin-$\beta$-hydroxydase is inhibited by the alcohol extract of Eschscholtzia (curve A) as well as by an aqueous solution of the freeze-dried extracts of Eschscholtzia and Corydalis (curve B) which leads to a reduction of the noradrenalin and adrenalin formation in the catecholamin metabolism. This inhibiting effect explains the sedative effect of the inventive pharmaceutical. The high concentration of dopamin which is maintained by the inhibition produces a positive influence in the case of Parkinsonism, a syndrome in which dopaminerg nerve cells are destroyed and the dopamin content in the brain must be kept high by synthetic administration.

3. Investigation of the mono-amino-oxidase reaction

As can be seen from FIG. 1, the concentration of dopa and/or dopamin is also regulated by its decomposition due to mono-amino oxidases. The mono-amino-oxidases convert primary amines with the aid of oxygen in the aqueous medium into the corresponding aldehyde, ammonia and hydrogen peroxide in the stoichiometric ratio. The amino-oxidase used here was obtained from the firm Sigma Chemicals. This amino-oxidase shows a high affinity for benzylamine as the substrate. Therefore the following investigations were carried out with benzylamine as the substrate and the influence of Corydalis and Eschscholtzia on the activity of this mono-amino-oxidase was tested.

The conversion of benzylamine into benzylaldehyde by the mono-amino-oxidase was proven photometrically and potentiometrically:

a) Photometrically, the proof is provided of the resultant benzaldehyde, which has a high molecular extinction coefficient ($1.2 \times 10^4$) at 241 nm. This sensitive proof permits the use of very small amounts of enzyme, which may be 0.01 and 0.02 U mono-amino-oxidase (MAO) in a reaction volume of 2 ml.

The respective test batch having a total volume of 2,000 $\mu$l contained:

50 $\mu$l of a 100 mM aqueous benzylamine.HCl-solution (corresponding to 2.5 mM), 100 mM phosphate buffer, pH 7.4, 0.01 U or 0.02 U MAO, added in 100 $\mu$l portions to a corresponding basic solution;

the reference cuvette contained buffer, water and benzylamine.

Figure 8:
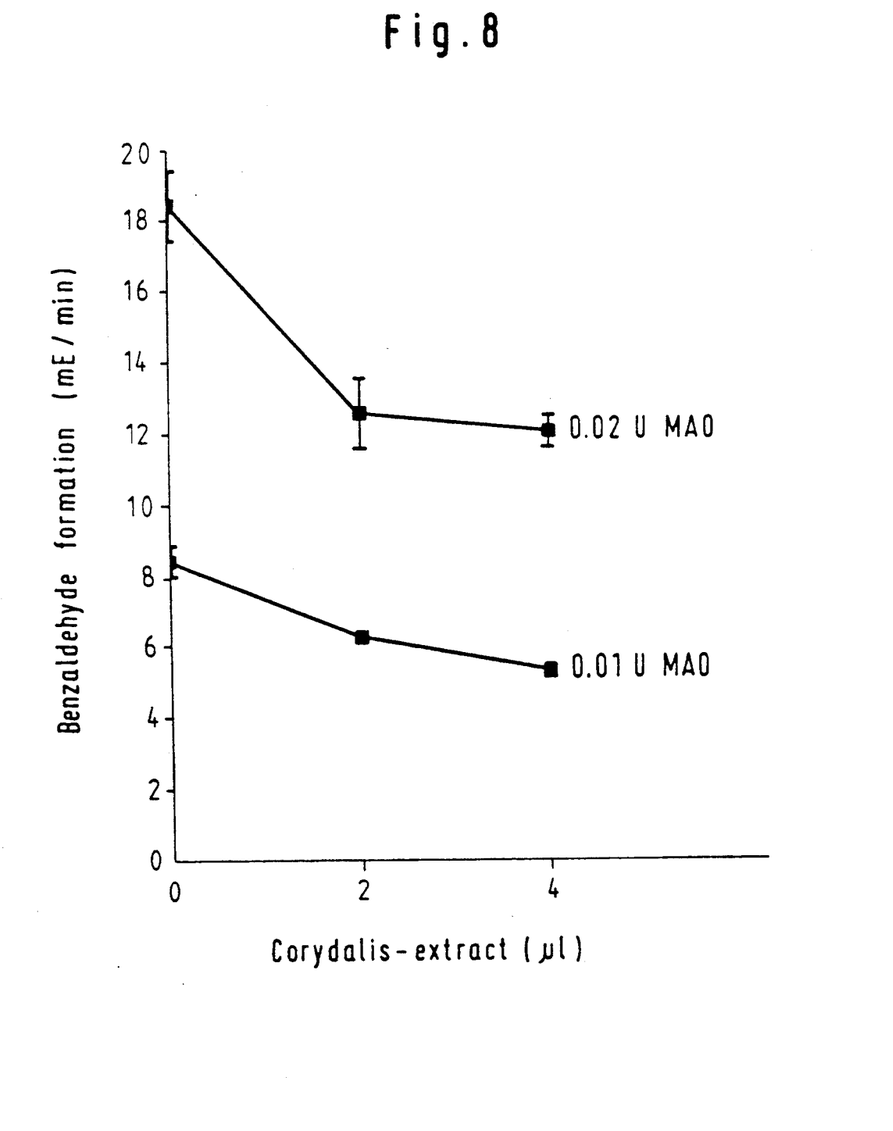
FIG. 8 shows photometrically at 241 nm the inhibition of the conversion reaction catalysed by an amino oxidase from benzylamine to benzaldehyde by Corydalis extract.

In the tests with the test batch described above, after 10 minutes reaction time the diluted extracts of Eschscholtzia and Corydalis were added to the measuring and reference cuvette and the altered activity was determined. FIG. 8 shows the inhibition of the benzaldehyde formation depending on the Corydalis concentration (20 or 40 $\mu$l of a 1:10 diluted solution of the basic extract).

Figure 9:
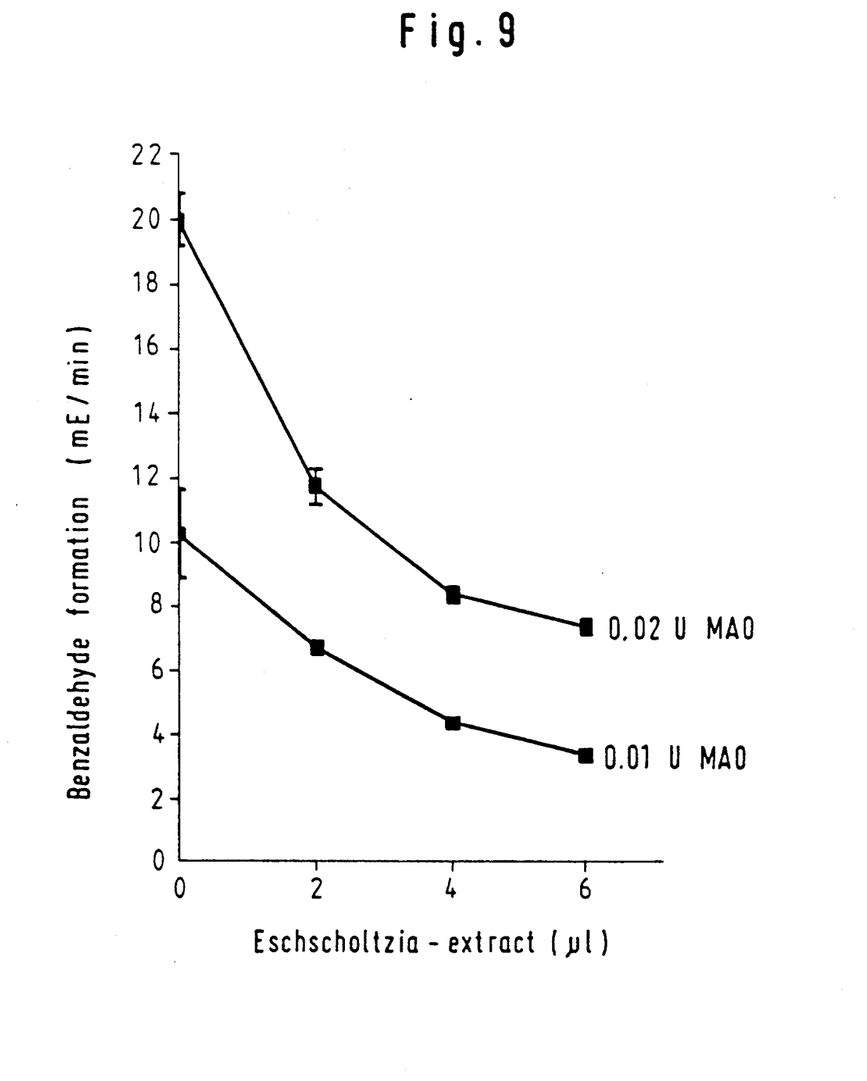
FIG. 9 reproduces the inhibition of the MAO-catalysed benzaldehyde formation at 241 nm depending on the concentration of the extract from Eschscholtzia.

FIG. 9 reproduces the inhibition of the extract of Eschscholtzia on the MAO activity with differing amounts of extract. Here a clear inhibition of the MAO activity is shown.

Figure 10:
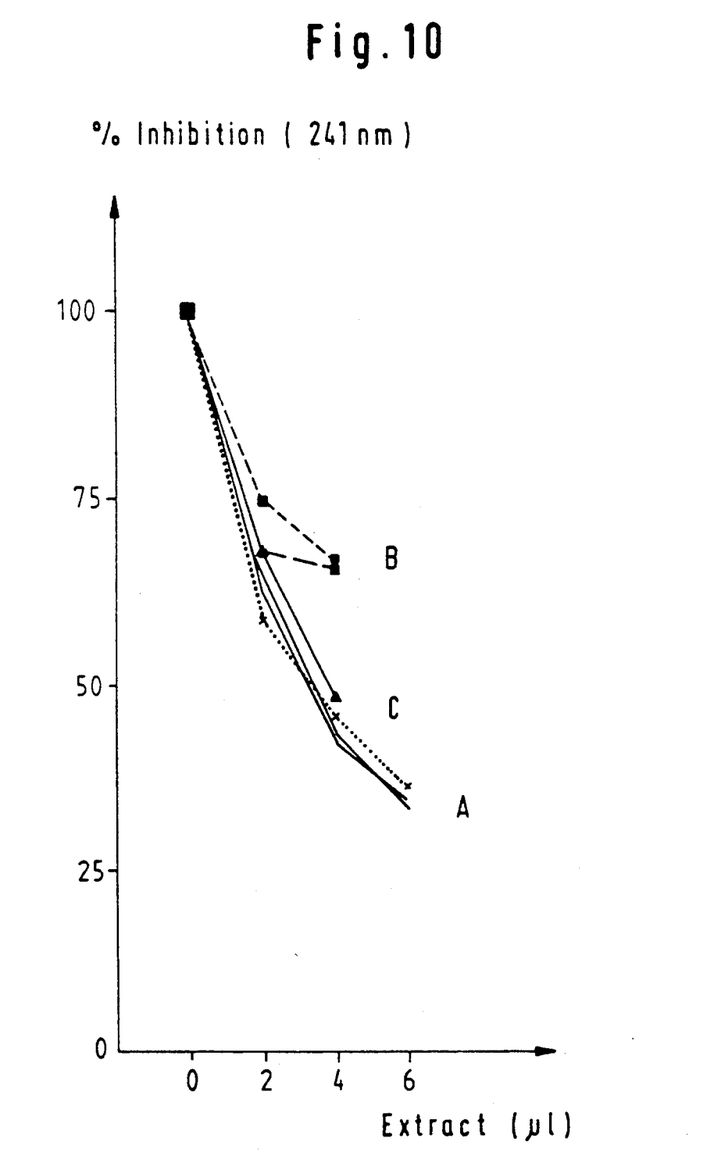
FIG. 10 shows the inhibition of the MAO-catalysed benzaldehyde formation at 241 nm by extracts of Eschscholtzia (A), Corydalis (B) as well as a mixture of the extracts of Corydalis and Eschscholtzia in the ratio 20:80.

FIG. 10 shows the inhibiting effect of MAO activity by the addition of different concentrations of Eschscholtzia extract (curve A), Corydalis extract (curve B) as well as of a mixture of the extracts of Corydalis and Eschscholtzia in the ratio 20:80 (curve C). For better comparison of the test results, the inhibiting effects are shown in percent in FIG. 10. The activity of the MAO was set as 100% in each test (on the basis of the viscous ammoniumsulfate-enzyme solution it was difficult to infer constant enzyme amounts of the product offered on the market).

The evaluation of the tests shows that a moderate inhibition of the MAO activity is caused by the Corydalis extract. A substantially greater influence is observed using the Eschscholtzia extract. Also significant is the MAO inhibition in the presence of a mixture of the two extracts, consisting of 80% Eschscholtzia and 20% Corydalis extracts.

b) By potentiometry, the reaction benzylamine+$O_2$+$H_2O \rightarrow$benzaldehyde+$NH_3$+$H_2O_2$ can be determined by the decrease in the oxygen content of the reaction solution using a platinum-oxygen electrode. The proof of the oxygen conversion demands larger amounts of substrate and enzyme. The respective test batch contained:

200 $\mu$l of a 100 mM benzylamine solution (corresponding to 10 mM), 1,000 $\mu$l of a 200 mM phosphate buffer solution, pH 7.5 (corresponding to 100 mM), 1,000 $\mu$l distilled water, 0.05 U MAO.

By adding 100 $\mu$l of the extract of Corydalis and Eschscholtzia, after 3 minutes reaction time the different rates of the oxygen conversion can be computed.

The results of the oxygen electrode show an activity reduction of the mono-amino-oxidase by the individual extracts of Corydalis and Eschscholtzia. The strong influence on the MAO activity by the Eschscholtzia extract was confirmed.

The tests above show that a significant inhibition of the MAO can be achieved by extracts of Corydalis and Eschscholtzia as well as by a mixture of these two extracts. Hence it can be inferred that when amino-oxidases are inhibited in the plasma in their activity, amines such as dopamine have a longer duration in the blood stream and therefore remain active longer. Hence the positive effect of the inventive pharmaceutical in the amelioration of states of agitation and nervous dysfunctions and the resultant depression states, especially in the case of dopamine deficiency syndromes, such as Parkinsonism, can be derived.

EXAMPLES

Example 1

Preparation of the Extract

Individual extracts of *Corydalis cavae rhizoma* and *Eschscholtzia californicae herba* were prepared. The preparation of the individual extracts was performed by extraction using percolation at 50° C. for 16 hours. A drug-extract ratio of 2.5:10 was maintained, i.e. from 2.5 g of the corresponding drug, 10 ml of the drug extract were obtained. Extraction agent: 30% by volume ethanol.

The extracts thus obtained can be used directly to prepare a pharmaceutical composition, or they can be transformed by lyophilisation into a dry extract.

Example 2

Influence of DL-dihydroxyphenylalanine on the Phenolase Reaction

Reaction conditions: phosphate buffer, pH = 6.5, 100 mM
tyrosin 2 mM
phenolase 20 U
DL-dihydroxyphenylalanine, variable

| t (min) | phenolase | | + DOPA 500 nM | | + DOPA 5 μM | | + DOPA 50 μM | |
|---|---|---|---|---|---|---|---|---|
| | mU | +/− | mU | +/− | mU | +/− | mU | +/− |
| 0  | 0   | 0    | 0   | 0   | 0   | 0   | 0    | 0   |
| 2  |     |      | 4   | 0   | 23  | 2.2 | 70   | 4.5 |
| 4  |     |      | 13  | 1.5 | 69  | 2.9 | 157  | 8.1 |
| 6  | 5   | 0.53 | 28  | 3.2 | 117 | 5.2 | 236  | 11  |
| 8  | 6   | 1.2  | 50  | 2.9 | 170 | 4.7 | 321  | 15  |
| 10 | 12  | 1.5  | 75  | 5.1 | 228 | 7.2 | 402  | 15  |
| 12 | 23  | 2.2  | ..  | ..  | ..  | ..  | ..   | ..  |
| 14 | 39  | 3.1  |     |     |     |     |      |     |
| 16 | 60  | 4.7  |     |     |     |     |      |     |
| 18 | 84  | 7.3  |     |     |     |     |      |     |
| 20 | 139 | 18   | 291 | 14  | 554 | 16  | 775  | 29  |
| .. | ..  | ..   | ..  | ..  | ..  | ..  | ..   | ..  |
| 30 | 404 | 32   | 562 | 28  | 883 | 21  | 1090 | 37  |

As FIG. 6 shows, DL-dopa can clearly shorten the lag phase of the phenolase, while 5 μM dopa already initiate an immediate dopachrome formation. With 50 μM dopa, the reaction proceeds directly after the start by the enzyme at the maximal reaction rate.

The autoxidation of dopa, i.e. a dopachrome formation without enzyme participation, is not found at pH=6.5 in the observed period.

However, DL-dopa is not any diol, but a substrate of the phenolase, whose product again produces dopachrome. Therefore below (example 3) comparative tests are made using 3,4-dihydroxybenzene.

Example 3

Influence of 3,4-dihydroxybenzene (as the Starter) on the Phenolase Reaction

Reaction condition: phosphate buffer, pH = 6.5, 100 mM
tyrosin 2 mM
phenolase 20 U
3,4-dihydroxybenzene, variable

| t (min) | phenolase | | + 3,4DHB 5 μM | | + 3,4-DHB 50 μM | |
|---|---|---|---|---|---|---|
| | mE | +/− | mE | +/− | mE | +/− |
| 0  | 0   | 0   | 0   | 0   | 0   | 0   |
| 2  |     |     | 6   | 1.7 | 27  | 2.7 |
| 4  |     |     | 15  | 1.3 | 63  | 4.8 |
| 6  | 8   | 0.91| 33  | 4.1 | 102 | 8.9 |
| 8  | 16  | 1.3 | 58  | 6.2 | 143 | 13  |
| 10 | 38  | 2.7 | 97  | 11  | 180 | 18  |
| .. | ..  | ..  | ..  | ..  | ..  | ..  |
| 20 | 312 | 14  | 355 | 42  | 446 | 42  |
| .. | ..  | ..  | ..  | ..  | ..  | ..  |
| 30 | 678 | 29  | 638 | 64  | 712 | 69  |

It is shown that o-dihydroxybenzene in concentration of 5 and 50 μM can shorter or suspend the lag phase of the phenolase reaction (FIG. 5).

Example 4 a) Detection of the Michaelis Constant for the Tyrosin Reaction by Phenoloxidase Reaction conditions: phosphate buffer, pH = 6.5, 100 mM
tyrosin 20 μM to 2 mM

| | phenolase 20 U/batch | |
|---|---|---|
| substrate concentration | reciprocal concentration 1/(M) | reciprocal concentration 1/(mE/min) |
| range 20 μM to 1 mM | | |
| 20 μM  | 0.05    | 0.27   |
| 40 μM  | 0.025   | 0.173  |
| 60 μM  | 0.0167  | 0.0116 |
| 80 μM  | 0.0125  | 0.098  |
| 100 μM | 0.01    | 0.076  |
| 500 μM | 0.002   | 0.044  |
| 1 mM   | 0.001   | 0.040  |
| $K_M$ = 141 μM | | |
| range 20 to 70 μM | | |
| 20 μM | 0.05  | 0.163 |
| 30 μM | 0.033 | 0.125 |
| 40 μM | 0.025 | 0.100 |
| 50 μM | 0.020 | 0.081 |
| 70 μM | 0.014 | 0.061 |
| $K_M$ = 145 μM | | |
| range 100 to 200 μM | | |
| 100 μM | 0.01   | 0.0555 |
| 120 μM | 0.0083 | 0.0525 |
| 140 μM | 0.0071 | 0.0475 |
| 160 μM | 0.0063 | 0.0435 |
| 180 μM | 0.0056 | 0.0415 |
| 200 μM | 0.005  | 0.40   |
| $K_M$ = 142 μM | | |
| range 1 to 2 mM | | |
| 1000 μM | 0.001   | 0.03352 |
| 1400 μM | 0.00071 | 0.0340  |
| 1800 μM | 0.00055 | 0.0334  |
| 2000 μM | 0.0005  | 0.0330  |
| $K_M$ = 137 μM | | |

The results are shown in FIGS. 4c to 4f.

b) Michaelis Constant of the Reaction with Corydalis Extract

The investigation of the reaction rate in the presence of Corydalis extract is carried out with dilution of the extract of 1:200. This extract amount led in the previous tests to an immediate start of the total enzyme activity, the initial phase amounts to 0 minutes.

The detected $K_M$ values show in the presence of Corydalis extract a somewhat higher dispersion, but they are in the same concentration range.

Michaelis Constants in the Presence of Corydalis Extract

Reaction conditions: phosphate buffer, pH = 6.5, 100 mM
tyrosin 20 μM to 2 mM
phenolase 20 U/batch
corydalis extract, 1:2000

| substrate concentration | reciprocal concentration 1/(M) | reciprocal reaction rate 1/(mE/min) | |
|---|---|---|---|
| range from 20 to 100 μM | | | |
| 20 μM | 0.05 | 0.0083 | 0.262 |
| 30 μM | 0.033 | 0.057 | |
| 40 μM | 0.025 | 0.045 | |
| 50 μM | 0.020 | 0.040 | |
| 60 μM | 0.017 | 0.033 | 0.110 |
| 70 μM | 0.014 | 0.030 | |
| 100 μM | | 0.080 | |
| $K_M =$ | | 164 μM | 137 μM |
| range 100 to 200 μM | | | |
| 100 μM | 0.01 | 0.0500 | |
| 120 μM | 0.0083 | 0.0435 | |
| 140 μM | 0.0071 | 0.0414 | |
| 160 μM | 0.0063 | 0.0383 | |
| 180 μM | 0.0056 | 0.0370 | |
| 200 μM | 0.005 | 0.0344 | |
| $K_M =$ | | 151 μM | |

Figure 4A:
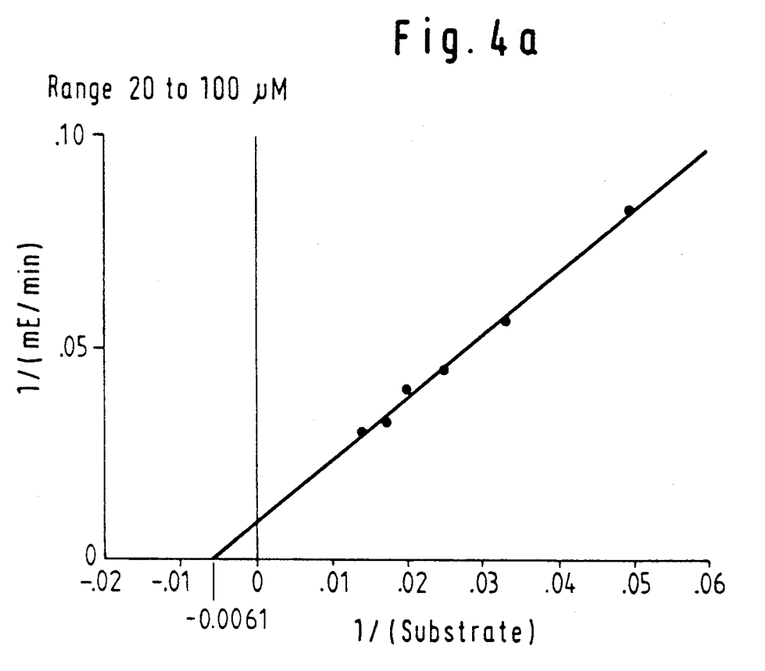
FIG. 4a–4f shows the Lineweaver-Burk-plot for the phenolase reaction with Corydalis extract (FIGS. 4a and 4b), as well as for comparison without Corydalis extract (FIGS. 4c to 4f).
Figure 4B:
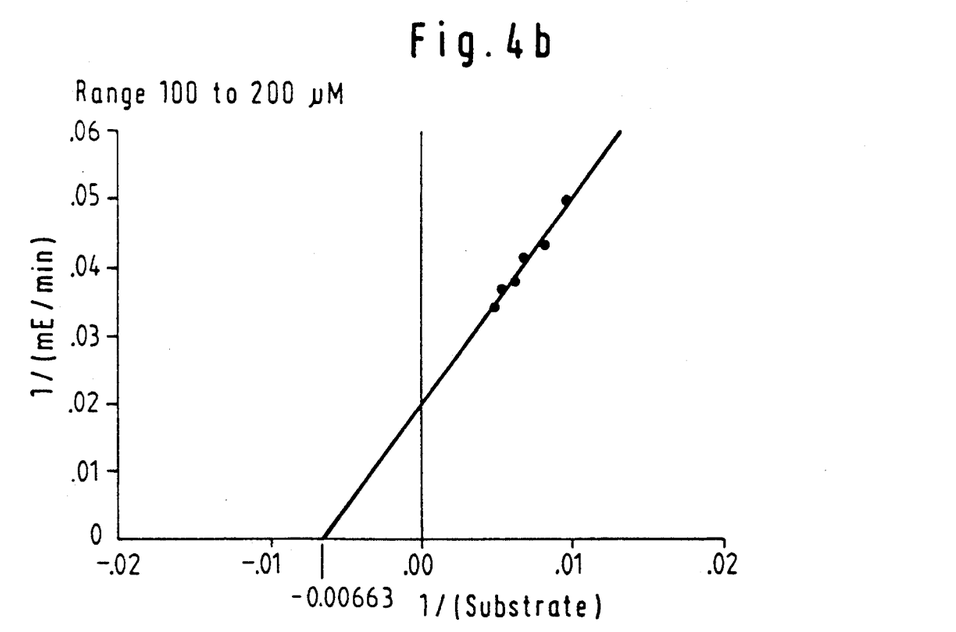
Figure 4C:
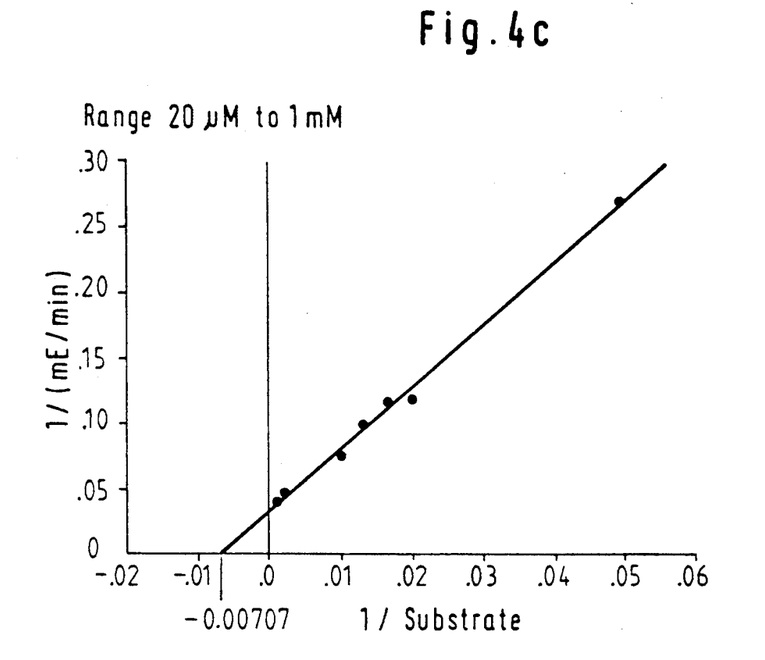
Figure 4D:
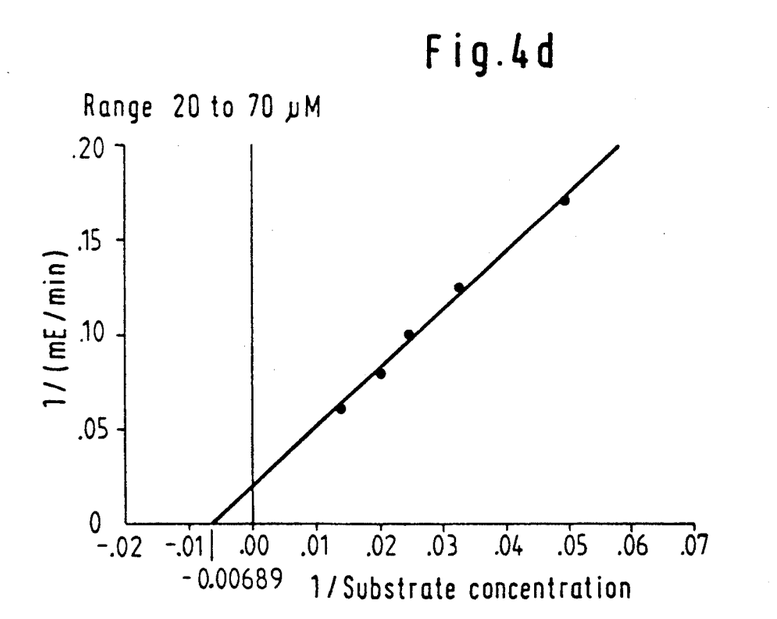
Figure 4E:
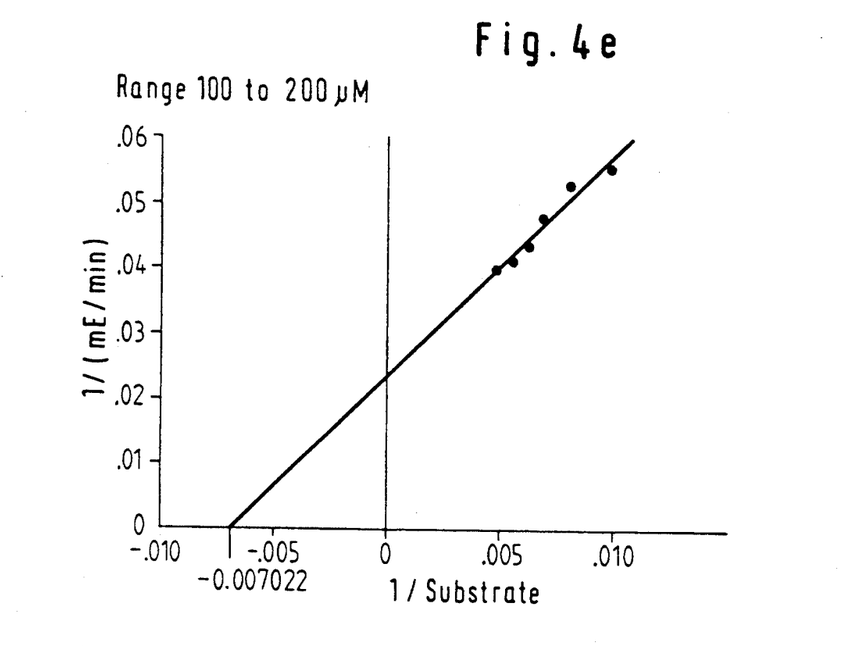
Figure 4F:
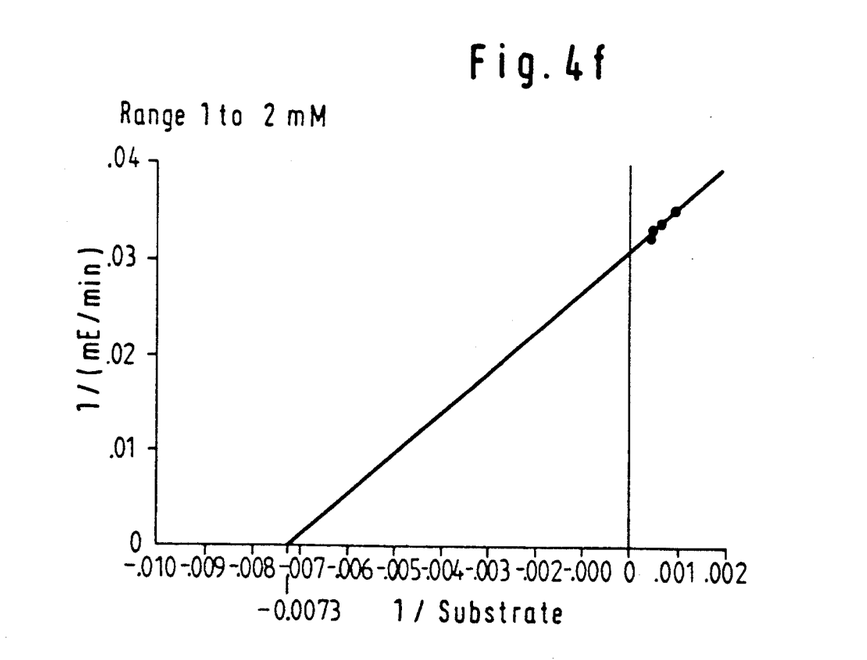

The results are shown in FIGS. 4a and 4b.

Example 5

Influence on MAO Activity a) Influence of the Corydalis extract:

As the table below and FIG. 8 show, the extract from Corydalis cava inhibits the activity of the MAO. 20 or 40 μl of a 1:10 diluted solution of the extract (2 or 4 μl of the original substance) are used. These amounts correspond, based on a total reaction volume of 2 ml, to a dilution of 1:1000 or 1:500. The absorption of the extract itself at 241 nm due to the presence of numerous aromatic compounds prevents the investigation of larger quantities of the extract, because then a zero balance of the reaction and reference cuvettes is no longer possible.

Activity of the MAO (mE/min) Under the Influence of Corydalis

Reaction conditions: phosphate buffer, pH = 7.4, 100 mM
benzylamine 2.5 mM
monoaminooxidase 0.01, 0.02 U/batch
corydalis extract, 1:10, variable
benzaldehyde (mE/min)

| | 0.01 U MAO: | 0.02 U MAO: |
|---|---|---|
| | 8.35 ± 0.50 (100%) | 18.4 ± 1.00 (100%) |
| +2 μl COR | 6.30 ± 0.02 (75%) | 12.6 ± 1.00 (68.5%) |
| +4 μl COR | 5.50 ± 0.00 (65.9%) | 12.2 ± 0.45 (66.3%) |

The results are shown in FIG. 8.

Example 6

Production of a Pharmaceutical Preparation a. Production of a tincture

To produce a tincture, the alcohol drug extracts obtained in accordance with example 1 were mixed, using 20 ml of the drug extract from *Corydalis cavae rhizoma* and 80 ml of the drug extract from *Eschscholtzia californicae herba*. 100 ml of a tincture ready for use are obtained.

b. Production of tablets

Extracts of *Corydalis cavae rhizoma* and *Eschscholtzia californicae herba* obtained as in example 1 were dried (e.g. lyophilized), and the dry extracts were mixed in a weight ratio Eschscholtzia/Corydalis=4/1 together with pulverized starch (as the pharmaceutical carrier substance) and were pressed in a tablet press to form tablets (0.5 g, diameter 0.6 cm). The proportion of active ingredient extracts in the tablets was 2% by weight.

b) Influence of the Eschscholtzia extract:

Because of the higher transparency of the Eschscholtzia extract, in this investigation 20, 40 and 60 μl of a 1:10 diluted solution can be used. Then a 1:1000, 1:500 or 1:330 diluted solution of the Eschscholtzia extract are found in the reaction batch.

The table below and FIG. 9 clarify the high inhibiting capacity of this extract: as from a dilution of 1:500, the activity of the monoaminooxidase is kept clearly below 50%, and with a dilution of 1:330, the activity of the enzyme is reduced to one third of the original value.

Activity of the MAO Under the Influence of Eschscholtzia

Reaction conditions: phosphate buffer, pH = 7.4, 100 mM
benzylamine 2.5 mM
monoaminooxidase 0.01, 0.02 U/batch
eschscholtzia extract, 1:10, variable
benzaldehyde (me/min)

| | MAO | |
|---|---|---|
| | 0.01 U | 0.02 U |
| | 10.3 +/− 1.50 (100%) | 20.0 +/− 0.30 (100%) |
| 2 μl ESCH | 6.75/0.25 (55.5%) | 11.8/0.55 (59%) |
| 4 μl ESCH | 4.50/0.00 (43.7%) | 8.50/0.30 (43.5%) |
| 6 μl ESCH | 3.50/0.00 (33.9%) | 7.50/0.30 (37.5%) |

The results are shown in FIG. 9.

We claim:

1. A pharmaceutical composition comprising a combination of an extract of Corydalis and an extract of Escholtzia, wherein both extracts are obtained by alcohol extraction, wherein the ratio of active ingredients in said extracts to said extracts is 2.5:10, wherein the weight ratio of the extract of Escholtzia to the extract of Corydalis in said composition is in the range of from about 20:1 to 1:1, and wherein said composition may additionally contain a pharmaceutically acceptable carrier.

2. The pharmaceutical composition of claim 1, wherein the extracts are in the form of an aqueous solution, an alcohol solution, or, in the form of a powder.

3. The pharmaceutical composition of claim 1, wherein the extracts are in the form of alcohol solution.

4. The pharmaceutical composition of claim 1, wherein said composition is in the form of an alcohol solution.

5. The pharmaceutical composition of claim 1, wherein the ratio of the extract of the Escholtzia to the extract of Corydalis in said composition is from about 10:1 to 2:1.

6. The pharmaceutical composition of claim 5, wherein the ratio of the extract of Escholtzia to the extract of Corydalis in said composition is 4:1.

7. The pharmaceutical composition of claim 1, wherein said corydalis is *Corydalis cavae rhizoma* and said escholtzia is *Escholtzia californicae herba*.

8. The pharmaceutical composition of claim 1, wherein said composition is an oral administration form.

9. The pharmaceutical composition of claim 1, wherein said composition is a form selected from the group consisting of a tablet, a dragee, a capsule and a tincture.

10. A method for ameliorating or suspending states of agitation and nervous dysfunctions, based on a disturbance of the amine balance, comprising administering to a subject afflicted with said states a pharmaceutically effective amount of a pharmaceutical composition comprising a combination of an extract of Corydalis and an extract of Escholtzia, wherein both extracts are obtained by alcohol extraction, wherein the ratio of active ingredients in said extracts to said extracts is 2.5:10, wherein the weight ratio of the extract of Escholtzia to the extract of Corydalis in said composition is in the range of from about 20:1 to 1:1.

11. The method of claim 10, wherein the states of agitation and nervous dysfunctions are caused by a reduced concentration of dopa/dopamine in the subject.

12. A method for ameliorating or suspending a state of depression, comprising administering to a subject afflicted with depression a pharmaceutically effective amount of a pharmaceutical composition comprising a combination of an extract of Corydalis and an extract of Escholtzia, wherein both extracts are obtained by alcohol extraction, wherein the ratio of active ingredients in said extracts to said extracts is 2.5:10, wherein the weight ratio of the extract of Escholtzia to the extract of Corydalis in said composition is in the range of from about 20:1 to 1:1.

13. A method for ameliorating the symptoms and side-effects of Parkinson's disease, comprising administering to a subject afflicted with Parkinson's disease a pharmaceutically effective amount of a pharmaceutical composition comprising a combination of an extract of Corydalis and an extract of Escholtzia, wherein both extracts are obtained by alcohol extraction, wherein the ratio of active ingredients in said extracts to said extracts is 2.5:10, wherein the weight ratio of the extract of Escholtzia to the extract of Corydalis in said composition is in the range of from about 20:1 to 1:1.

* * * * *